United States Patent [19]

Aledo et al.

[11] Patent Number: 4,850,988
[45] Date of Patent: Jul. 25, 1989

[54] DOUBLE FASTENING SYSTEM WITH A SLIT

[75] Inventors: Eduardo C. A. Aledo; Philippe Pommez, both of Sao Paulo, Brazil

[73] Assignee: Chicopee, New Brunswick, N.J.

[21] Appl. No.: 18,646

[22] Filed: Feb. 25, 1987

[51] Int. Cl.[4] .......................................... A61F 13/16
[52] U.S. Cl. .................................. 604/385.1; 604/389
[58] Field of Search ................. 604/385.1, 385.2, 386, 604/389, 390, 391, 387; 2/219-221

[56] References Cited

U.S. PATENT DOCUMENTS

| | | | |
|---|---|---|---|
| 2,294,617 | 9/1942 | Horowitz | 604/386 |
| 2,834,347 | 5/1958 | Connally | 604/385.1 |
| 3,983,876 | 10/1976 | Cepuritis | 604/390 |
| 3,990,449 | 11/1976 | Cheslow | 604/390 |
| 4,010,754 | 3/1977 | Pieniak | 604/385.2 |
| 4,034,752 | 7/1977 | Tritsch | 604/390 |
| 4,090,516 | 5/1978 | Schaar | 604/390 |
| 4,209,016 | 6/1980 | Schaar | 604/390 |
| 4,410,326 | 12/1983 | Dussaud et al. | 604/390 |
| 4,500,316 | 2/1985 | Damico | 604/385.1 |
| 4,753,650 | 6/1988 | Williams | 604/389 |

FOREIGN PATENT DOCUMENTS

| | | | |
|---|---|---|---|
| 0577229 | 6/1959 | Canada | 604/386 |
| 0170239 | 4/1956 | Sweden | 604/386 |

Primary Examiner—C. Fred Rosenbaum
Assistant Examiner—Sharon Rose
Attorney, Agent, or Firm—Lawrence D. Schuler

[57] ABSTRACT

A double fastening system with a slit for using in disposable articles such as disposable diapers having a backing sheet, a liquid permeable cover and an absorbent core disposed therebetween. The fastening system comprises two adhesive regions (15, 16) symmetrically opposite with relation to the longitudinal axis (Y—Y) of the disposable article and applied to the exposed surface of the liquid permeable cover, regions (15, 16) being separated by a slit (17), parallel to the transversal axis (X—X) of such article.

7 Claims, 4 Drawing Sheets

DOUBLE FASTENING SYSTEM WITH A SLIT

The present invention refers to a fastening system and more precisely to a double fastening system with a slit for disposable articles such as disposable diapers.

BACKGROUND OF THE INVENTION

Conventional prior art is mainly based on the use of adhesive tapes for closing or fastening diapers, especially disposable diapers, around the waist of the wearer. In addition, the prior art has provided sealing systems to prevent fluid from leaking from the diaper in the regions around the wearer's thighs and waist. Sealing systems which help prevent leakage in the thigh regions comprise elastic elements, such as elastic bands or one or more elastic strands, which are secured in the generally central portions of the side margins of the diaper.

Sealing systems which help prevent leakage of liquid at the waist of the wearer comprise elastic elements which are secured in the upper and/or lower margins of the diaper to provide a so-called "elasticized waistband" diaper. In the prior art, the aforementioned fastening or closure system and the aforementioned sealing system are interdependent and allowed, relative motion between the wearer's body and the diaper itself. This produced bagginess which in turn led to leakage of liquid especially at the leg regions of the diaper.

The present invention is directed to providing a closure system which allows a better fitting of such article to the user, thus reducing risks of leakage by combining such closure system and elastic system.

SUMMARY OF THE INVENTION

One object of the present invention is to interrupt the force-transmitting continuous surface which occurs in one-adhesive-region systems, by providing a cut at such adhesive region, which allows the resulting two adhesive regions to work independently from another one.

Another object is to provide a better fitting of a diaper around the thighs and waist regions, which vary with the user's ergonomic characteristics, thus allowing the legs to move without also moving the diaper relative to the body.

Another advantage is the additional option for closing and fitting such article to the body, each of the aforesaid adhesive regions being adapted to be used independently from the other.

In accordance with the present invention there is provided a closure system for a disposable article such as a disposable diaper, said closure system comprising two adhesive regions, symmetrically opposite with relation to the longitudinal axis of the article and applied on the outer corners of the liquid permeable covering of the article, said regions being separated by a slit which is generally parallel to the transverse axis of the article or which extends inwardly from the side margin of the diaper toward a generally central region thereof.

BRIEF DESCRIPTION OF THE DRAWINGS

The invention can be better understood with reference to the following detailed description together with the appended drawings in which.

DETAILED DESCRIPTION OF THE INVENTION

Figure 1:
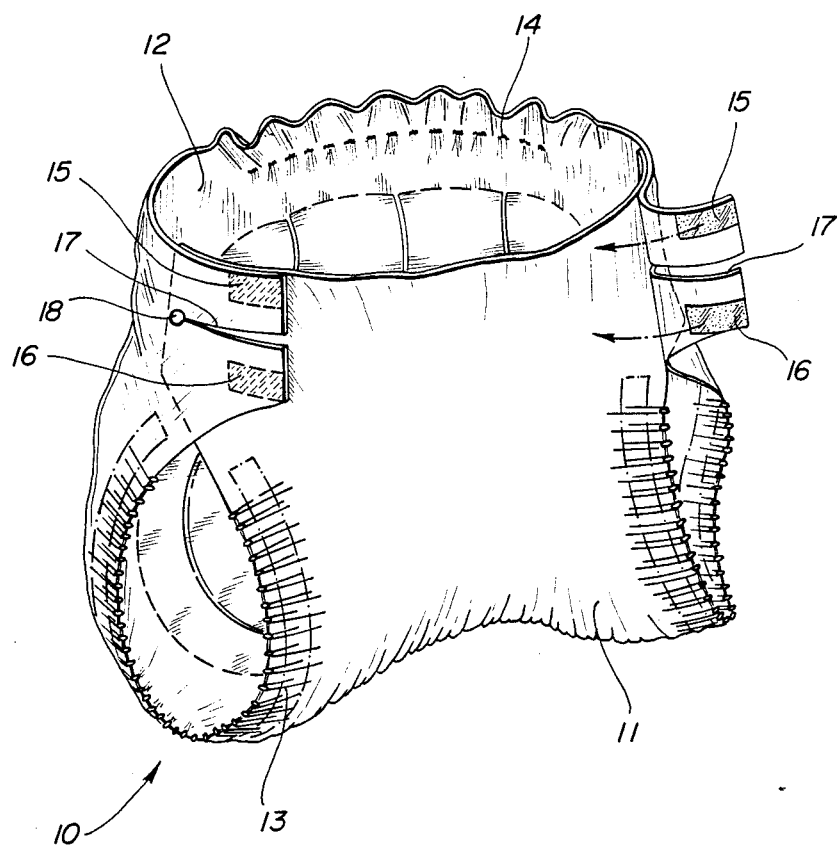
FIG. 1 is a perspective view of a diaper provided with the closure system of the present invention.
Figure 2:
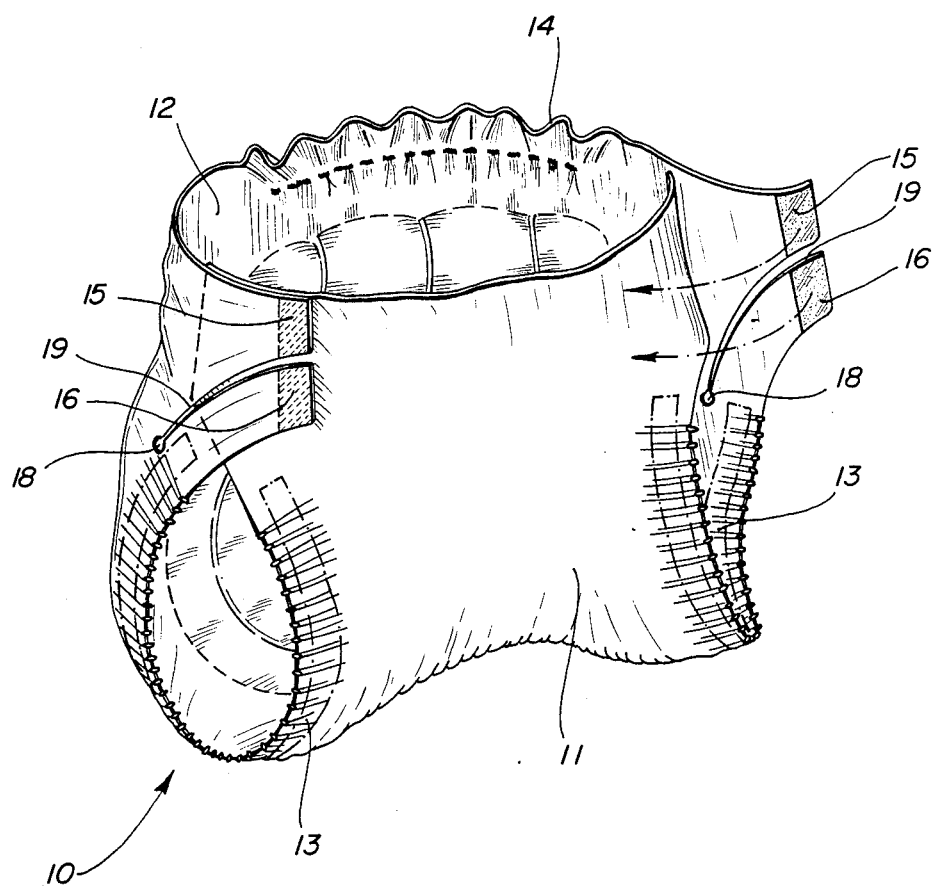
FIG. 2 is a perspective view illustrating another embodiment of said closure system.
Figure 3:
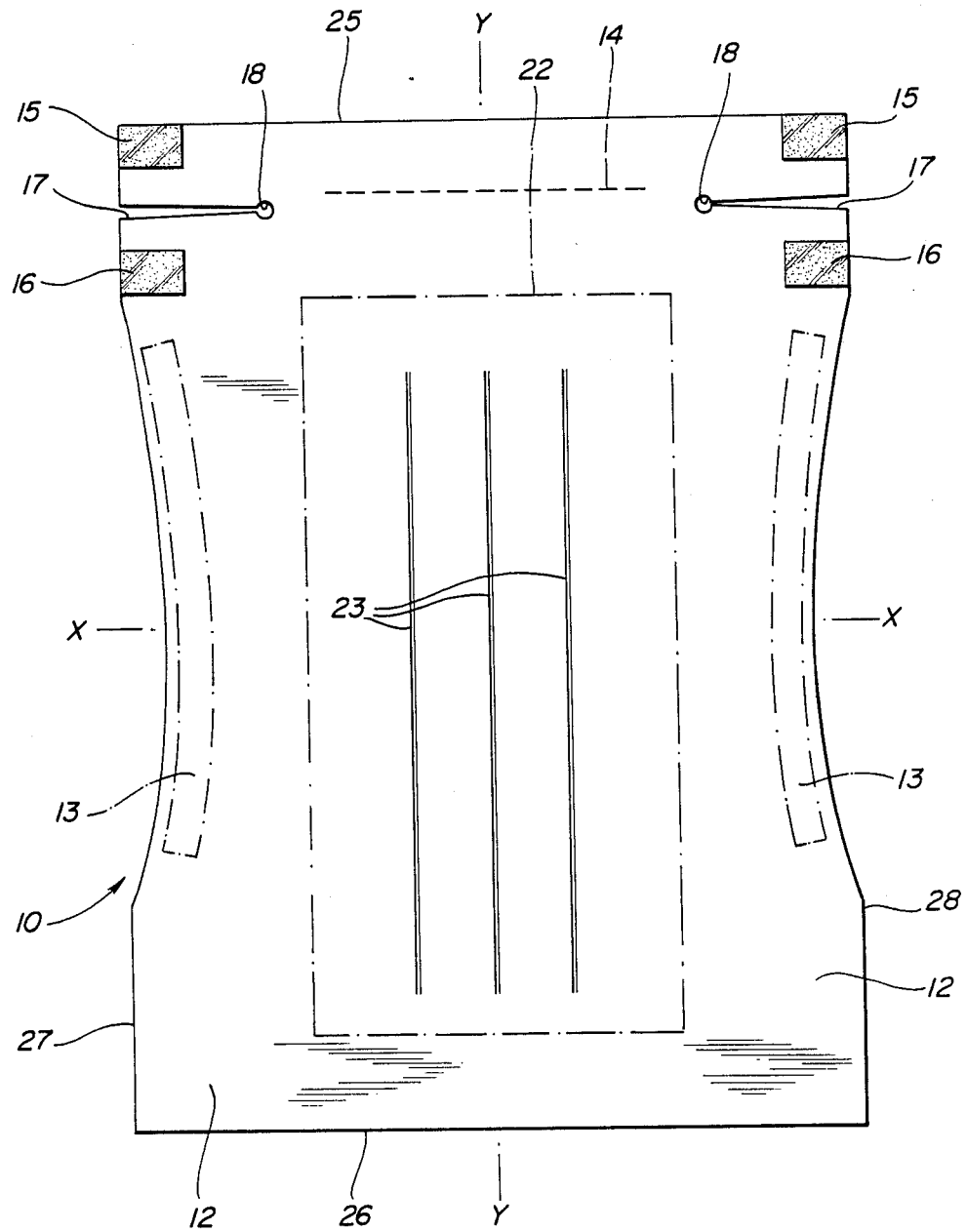
FIG. 3 is a front plan view of the diaper illustrated in FIG. 1.

Referring now to the drawings, there is shown a diaper 10 having a liquid-impermeable backing sheet 11, a liquid-permeable facing sheet or covering 12 and an absorbent core 22 disposed between said backing sheet and said covering. The diaper further comprises an elastic element 13 in the central portion of each of the side margins of the diaper and an elastic element 14 in the central region of the top margin of the diaper. Backing sheet 11 may comprise a film of polyethylene or other liquid-impermeable material. Covering 12 may be a nonwoven fabric, highly porous paper or similar material which permits passage of liquid therethrough to the underlying absorbent core. The absorbent core 22 may comprise, e.g. comminuted wood pulp or other material having good liquid absorbency. Elastic elements 13 and 14 may be elastic monofilaments or a tape of heat shrinkable material which, after heat shrinking, has elastic properties. In the embodiment under discussion, elastic element 14 is preferably in the form of an elastic monofilament which, as seen in FIG. 3, is secured while in a stretched state between backing sheet 11 and covering 12. When subsequently relaxed, elastic element 14 serves to gather the material along the upper margin of the diaper as shown in FIGS. 1 and 2. Elastic elements 13, 13 at the opposed side margins of the diaper are preferably in the form of a tape of heat shrinkable material which, after application of heat thereto, displays elastic properties. Suitably sized lengths of the heat shrinkable material are secured in the side margins of diaper 10 between backing sheet 11 and cover 12 as shown in FIG. 3. The side margins of the diaper are subsequently heated as a result of which the tapes of heat shrinkable material shrink to provide the gathered side margins, shown in FIGS. 1 and 2, which encircle the thighs of the wearer during use. Since, as mentioned above, the tapes have elastic properties after their heat treatment, the gathered portions in the side margins of the diaper are extensible so as to fit comfortably around the thigh regions of the wearer and provide a gasketing effect to prevent the leakage of fluid.

It will be recognized that elastic element 14 may comprise two or more elastic monofilaments rather than the single strand illustrated in the drawings. Alternatively, pieces of the aforementioned heat shrinkable tape material could be used as elastic element 14 in the upper margin of the diaper. Similarly, the heat shrinkable tapes comprising elastic elements 13, 13 at the side margins of the diaper could be replaced by one or more elastic monofilaments.

While in diaper 10 illustrated in the drawings, absorbent core 22 is smaller in size that the backing and facing sheets, it will be understood that core 22 can assume various sizes and shapes. Absorbent core 22 can be stabilized, e.g. by embossing along lines 23, as shown in FIG. 3. It will be understood by those skilled in the art that is diaper 10 illustrated in the drawings, backing sheet 11 and facing sheet 12 may be secured to each other, e.g. with a suitable adhesive or by heating sealing, at the marginal portions of the diaper. When the backing and facing sheets are joined around the margins of the diaper in the fashion just mentioned, the absorbent core is prevented from moving; however, the absorbent core may be further secured against undesirable movement by gluing it to the underlying backing sheet.

Two distinctive adhesive regions 15 and 16 are provided on the inner surface (i.e. that surface which faces the reader in FIG. 3 and which contacts the body of the wearer when the diaper is in use) of liquid-permeable covering 12, at each of the upper corners of the diaper, generally adjacent the ends of elastic element 14. As can be seen in FIG. 3, adhesive regions 15, 16 are placed symmetrically with respect to the longitudinal axis, Y—Y, of diaper 10 near the upper corners of the diaper.

The adhesive used for regions 15 and 16 may be of the pressure sensitive acrylic type or any other type well-known in the art. Preferably, the adhesive is of the type which can be readily released from the outer surface of backing sheet 11 without undue damage to the backing sheet or the adhesive. When this type of adhesive is used, it is an easy matter to release the adhesive coated portions of the diaper from engagement with the backing sheet when it is desired to adjust the fit of diaper or remove it from the wearer. If the adhesive used for regions 15, 16 is not readily releasable from the outer surface of the backing sheet, then those portions of the backing sheet which will normally be contacted by the adhesive portions may be suitably treated, by methods known to those skilled in the art, to provide the necessary easy-release characteristics. The adhesive ultimately chosen for use may be applied in any convenient manner, e.g. by an adhesive transfer process.

The preferred embodiment illustrated in FIG. 3 comprises a pair of generally rectangular first adhesive regions 15, there being one such adhesive region at each upper corner of the diaper. Thus, each of first adhesive regions 15 is located in the upper margin of the diaper adjacent upper edge 25 and adjacent one of the opposed side edges of the diaper. Diaper 10 further comprises a pair of generally rectangular second adhesive regions 16, each of which is spaced downwardly from upper edge 25 of the diaper and from its associated first adhesive region 15. Each such second adhesive area 16 is located, as can be seen in FIG. 3, adjacent one of the side edges of the diaper.

Adhesive regions 15 and 16 at each side of the diaper are separated by a slit 17 running from a side edge of the diaper toward the central region thereof and generally parallel to the transverse axis, X—X, of the diaper.

In the preferred embodiment, each slit 17 extends farther inwardly from its respective side edge than do its associated adhesive regions 15, 16. Each slit 17 terminates at its interiorly located end in a circular cutout 18 which helps prevent undesirable tearing of the diaper by distributing forces applied thereto along such circular surface. As illustrated in FIG. 3, there is an adhesive free region between slit 17 and the lower edge of the first adhesive region 15 and an adhesive free region between slit 17 and the upper edge of second adhesive region 16.

In use, a child to be diapered is positioned facing upwardly on top of the diaper in the generally flat configuration shown in FIG. 3 so that the child's buttocks are disposed more or less centrally of the diaper. The lower part of the diaper is brought up between the child's leg so that lower edge 26 is in alignment with upper edge 25. Adhesive areas 15, 15 at upper edge 25 are adhered to the backing sheet at the corner regions where side edges 27 and 28 meet lower edge 26 (arrow A in FIG. 1). This action fixes the diaper in position around the child's waist. Adhesive regions 16, 16 at each side of the diaper are manipulated to conform the diaper around the thighs of the child and are then secured to the impermeable backing sheet 18 (arrow B in FIG. 1). The diaper prior to closing adhesive regions 15, 16 is illustrated at the right hand side of FIG. 1; the diaper after securing adhesive regions 15, 16 to the backing sheet is illustrated at the left hand side of FIG. 1.

As indicated earlier herein and as just described, the operation of closing and fastening the diaper of the present invention around the waist of the wearer (using adhesive regions 15, 15) can be accomplished independently of the operation of adjusting the fit of the diaper around the thighs (using adhesive regions 16, 16) so as to most effectively seal the diaper from undesirable leakage. With the diaper of the present invention, a movement of the user's leg in one direction will pull the diaper and elastic portion around the thigh to the same direction and cause the diaper to follow the body. There is less relative movement of the body and the diaper with respect to each other. This reduces the amount of "gapping" between the thighs of the wearer and the diaper itself so that the possibility of leakage is reduced.

In another embodiment, illustrated in FIG. 2, an arcuate slit 19, similar to slit 17, separates adhesive regions 15 and 16 at each side of the diaper and extends inwardly and downwardly from the side margin to terminate near the upper end of elastic element 13. Arcuate slit 19 terminates in a circular cutout 18 which prevents the diaper from tearing when stresses are applied in the regions surrounding the slit. In this embodiment, there are no adhesive-free portions between adhesive region 15 and slit 19 or between adhesive region 16 and slit 19.

It will be understood the slits 17 and 19 allow the diaper to be fitted and closed around the waist of the wearer (using adhesive regions 15, 15) and to be fitted and sealed against leakage at the thighs (using adhesive regions 16, 16) in separate, independent steps.

Figure 4:
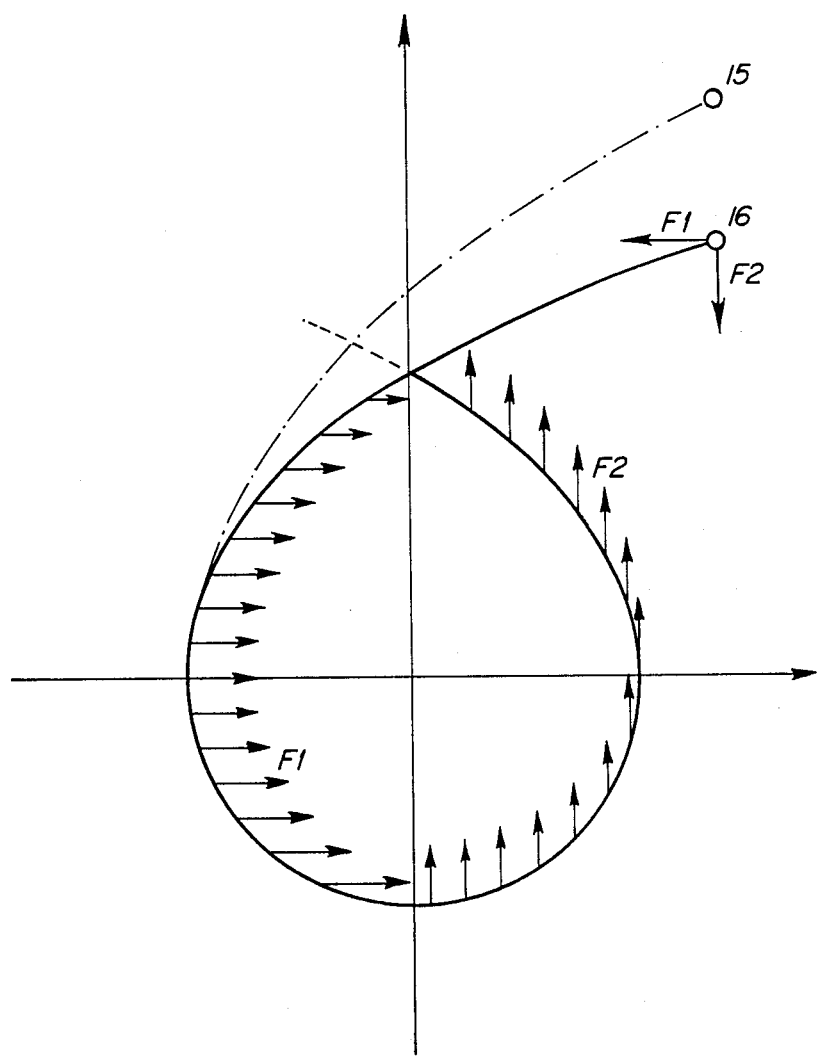
FIG. 4 is a scheme of actuating forces in the system of the present invention.

FIG. 4 illustrates the scheme of actuating forces in the fastening system with a slit, wherein dot 15 represents the adhesive region 15 for fitting the diaper around the waist and dot 16 represents the adhesive region 16 for fitting the diaper to the legs. Arrows F1 and F2 are possible exertions applied at the adhesive region.

It should be understood that the present invention is not limited to the descriptions and illustrations of the disclosed embodiments, thus being likely to be achieved in different ways, however, within the scope of the following claims.

What is claimed is:

1. A disposable article comprising:
   a liquid impermeable backing sheet;
   a liquid permeable covering sheet, said covering sheet having a surface which contacts the body of the wearer when the disposable article is in use;
   an absorbent core disposed between said backing sheet and said covering sheet;
   an upper edge;
   an upper marginal portion adjacent said upper edge;
   a lower edge;
   a lower marginal portion adjacent said lower edge;
   a pair of side edges, each of said side edges having a side marginal portion adjacent thereto;
   a transverse axis lying between said upper edge and said lower edge and a longitudinal axis lying between said side edges; said transverse and longitudinal axes being mutually perpendicular and intersecting in a central region of the disposable article;

a first upper corner in the region where said upper edge meets a first of said side edges;

a second upper corner in the region where said upper edge meets the second of said side edges;

said backing sheet being secured to said covering sheet in said marginal portions;

said disposable article comprising first adhesive means applied to the body contacting surface of said covering sheet in the upper marginal portion of said diaper near each of said upper corners;

said disposable article further comprising second adhesive means applied to the body contacting surface of said covering sheet in each of the marginal portions of said disposable article, each of said second adhesive means being spaced downwardly from its associated first adhesive means toward said transverse axis;

said first and second adhesive means at each side of the disposable article being separated by a slit cut through said backing sheet and said covering sheet and running from their associated side edge toward the longitudinal axis of the disposable article.

2. A disposable article according to claim 1 wherein each of said slits run substantially parallel to said transverse axis.

3. A disposable article according to claim 2 wherein said slits terminate in a circular cutout.

4. A disposable article according to claim 1 wherein each of said slits is arcuate in configuration and runs inwardly and downwardly toward the central region of the disposable article.

5. A disposable article according to claim 4 wherein said slits terminate in a circular cutout.

6. A disposable article according to any one of claims 1-5 further comprising elastic elements in the central portions of each of said side edges.

7. A disposable article according to any one of claims 1-5 further comprising elastic elements in the central portion of each of said side edges and an elastic element in said upper marginal portion.

* * * * *